US010889654B2

(12) United States Patent
Hummel et al.

(10) Patent No.: US 10,889,654 B2
(45) Date of Patent: Jan. 12, 2021

(54) ACYLATION PROCESS

(71) Applicant: SOLVAY ACETOW GmbH, Freiburg (DE)

(72) Inventors: Andreas Hummel, Freiburg (DE); Hans-Juergen Ehret, Freiburg (DE)

(73) Assignee: SOLVAY ACETOW GmbH, Freiburg (DE)

( * ) Notice: Subject to any disclaimer, the term of this patent is extended or adjusted under 35 U.S.C. 154(b) by 0 days.

(21) Appl. No.: 15/027,366

(22) PCT Filed: Oct. 8, 2014

(86) PCT No.: PCT/EP2014/071573
§ 371 (c)(1),
(2) Date: Apr. 5, 2016

(87) PCT Pub. No.: WO2015/052255
PCT Pub. Date: Apr. 16, 2015

(65) Prior Publication Data
US 2016/0237172 A1 Aug. 18, 2016

(30) Foreign Application Priority Data
Oct. 10, 2013 (EP) .................................. 13188120

(51) Int. Cl.
*C08B 3/06* (2006.01)
*C08B 31/04* (2006.01)
*C08B 37/00* (2006.01)
*C02F 1/44* (2006.01)
*C07C 51/487* (2006.01)
*C08B 3/28* (2006.01)
*C02F 101/30* (2006.01)
*C02F 103/28* (2006.01)

(52) U.S. Cl.
CPC .................. *C08B 3/06* (2013.01); *C02F 1/44* (2013.01); *C07C 51/487* (2013.01); *C08B 3/28* (2013.01); *C08B 31/04* (2013.01); *C08B 37/00* (2013.01); *C02F 2101/30* (2013.01); *C02F 2103/28* (2013.01)

(58) Field of Classification Search
CPC . C08B 3/28; C07C 51/487; C02F 1/44; C02F 2101/30
USPC ........................................................ 536/76
See application file for complete search history.

(56) References Cited

U.S. PATENT DOCUMENTS

| 2,300,180 | A | * | 10/1942 | Schulze | .................... C08B 3/22 536/81 |
| 5,656,292 | A | | 8/1997 | Urtti et al. | |
| 2002/0148768 | A1 | * | 10/2002 | Nasser, Jr. | ............. B01D 61/04 210/321.6 |
| 2006/0004192 | A1 | | 1/2006 | Oya et al. | |
| 2006/0066011 | A1 | | 3/2006 | Oya | |
| 2008/0003443 | A1 | * | 1/2008 | Oya | ........................ B29C 41/24 428/532 |
| 2011/0143067 | A1 | | 6/2011 | Hölter et al. | |
| 2013/0340814 | A1 | | 12/2013 | Lahary | |

FOREIGN PATENT DOCUMENTS

| EP | 1619209 | A1 | 1/2006 |
| EP | 2075261 | A1 | 7/2009 |
| JP | 2008007746 | A | 1/2008 |
| JP | 2008031396 | A | 2/2008 |
| JP | 2008056890 | A | 3/2008 |
| JP | 2008069240 | A | 3/2008 |
| WO | 9702018 | A1 | 1/1997 |
| WO | 0105839 | A1 | 1/2001 |
| WO | 2010017989 | A1 | 2/2010 |
| WO | 2012084898 | A1 | 6/2012 |

OTHER PUBLICATIONS

Brown ('A Convenient Preparation of Volatile Acid Chlorides'; [Contribution From the George Herbert Jones Laboratory of the University of Chicago]; Jun. 1938, vol. 60, pp. 1325-1328).*
Teella, Achyuta Vara Prasada Rao, "Separation of Carboxylic Acids From Aqueous Fraction of Fast Pyrolysis Bio-Oils Using Nanofiltration and Reverse Osmosis Membranes" (2011). Open Access Dissertations. 485.; https://scholarworks.umass.edu/open_access_dissertations/485.*
Han et al. (Journal of Membrane Science 107 (1995) 107-113).*
A. Hummel, "Industrial processes", Macromolecular Symposia, 2004, vol. 208(1), pp. 61-80.
International Search Report and Written Opinion dated Dec. 23, 2014 for PCT/EP2014/071573 to SOLVAY ACETOW GmbH filed Oct. 8, 2014.

* cited by examiner

Primary Examiner — Shaojia A Jiang
Assistant Examiner — Michael C Henry
(74) Attorney, Agent, or Firm — Vorys, Sater, Seymour & Pease

(57) ABSTRACT

The invention concerns a process for the manufacture of an acylated polysaccharide which comprises. (a) reacting a polysaccharide with an acylating agent to produce an acylated polysaccharide and (b) washing the acylated polysaccharide with water containing from 0.05 to 15 mg/l $Ca^{2+}$-ions (c) recovering the washed acylated polysaccharide and an aqueous phase containing carboxylic acid from step (b).

24 Claims, No Drawings

ACYLATION PROCESS

This application claims priority to European application No. 13188120.3, the whole content of this application being incorporated herein by reference for all purposes.

Acylated polysaccharides, like acetylated cellulose or starch, are important processed renewable raw materials which can be used in a wide range of industrially applied polymers, applied for example in filter manufacturing (e.g. WO2010017989), pharmaceuticals (e.g. WO9702018) and polymeric layers for photovoltaic modules (e.g. WO2012084898).

A common process for the acylation of polysaccharides is the reaction of polysaccharides with an acylation agent, for example a carboxylic acid anhydride, which reacts with the hydroxylfunctions of the polysaccharides to form the polysaccharide ester, i.e. acylated polysaccharides. The free acid which is formed in this reaction from the carboxylic acid anhydride, and other reactants, catalysts, solvents optionally being employed and by-products formed, are suitably removed in order to recover the acylated polysaccharide. It is an objective of this invention to by provide an improved polysaccharide acylation process.

WO 01/05839 describes the removal of organic impurities like hemicelluloses from solutions containing acetic acid derivatives, employing surface-active agents, in particular lignosulfonates. The surface active agents prevent agglomeration of impurities on the concentration side of the membrane, therefore avoiding fouling of filtration membranes in the process of recovering acetic acid derivatives from an aqueous waste stream from a process to obtain cellulose acetate.

It was now found that before filtration (e.g. nanofiltration or reverse osmosis) of aqueous waste streams from a polysaccharide acylation process, in particular the acetylation of cellulose with acetic acid anhydride, in order to remove organic impurities e.g. hemicellulose, addition of lignosulfates or other surface active agents is not necessary if water having a low content of $Ca^{2+}$-ions is used in the process. Consequently the invention concerns a process for the manufacture of an acylated polysaccharide which comprises
  (a) reacting a polysaccharide with an acylating agent to produce an acylated polysaccharide and
  (b) washing the acylated polysaccharide with water containing from 0.05 to 15 mg/l $Ca^{2+}$-ions.
  (c) recovering the washed acylated polysaccharide and an aqueous phase containing carboxylic acid from step (b).

The process according to the invention is generally operated in the substantial or complete absence of surface active agents. Such surfactant agent may comprise anionic surfactants like lignosulfonates or alkyl(ether)phosphates, non-ionic surfactants such as alcohol ethoxylates like octyl phenol ethoxylate or sodium tetradecyl sulphate, cationic surfactants such as quarternary ammonium compounds, or amphoteric surfactants like iminodipropionates. Particularly, the surface active agents which are substantially or completely absent in the process according to the invention are lignosulfonates.

If washing water with a $Ca^{2+}$-ion content in accordance with this invention is used, the aqueous solution from the acylated polysaccharide workup can be subjected to nanofiltration or reverse osmosis without residues clogging the nanofiltration or reverse osmosis membrane, or obstructing other equipment used in the further process. Solvents, excess reactants or valuable by-products such as carboxylic acids can be efficiently recovered in desirable purities allowing notably in view of recycling thereof to the acylation process. In the preferred process, the aqueous solution, containing from 10 to 40 wt. % acetic acid which results from washing the cellulose acetate and which is subject to further recycling, can be filtered prior to further use to remove organic impurities without clogging of the filtration membrane, even at high volume reductions of up to 99%.

The term "acylation of polysaccharides" is intended to denote the reaction of free hydroxylgroups of polysaccharides (PS) with an acylation agent A to form a corresponding acylated polysaccharide. Particular polysaccharides correspond to formula $PS(OH)_3$ and react with the acylation agent to an acylated polysaccharide of formula $PS(OH)_{3-x}(OCOR)_x$. In the formula $PS(OH)_{3-x}(OCOR)_x$, x denotes the DS (degree of substitution) of the hydroxyl groups in the polysaccharide. The DS is the average amount of acylated hydroxyl groups per monosaccharide entity. The DS is usually from 0.5 to 3.

According to the present invention, R is an aliphatic or cycloaliphatic radical containing 1 to 18 carbon atoms, an araliphatic radical containing 7 to 12 carbon atoms, an aromatic radical containing 6 to 12 carbon atoms. R can optionally be substituted by one or more halogens, preferably fluorine, $NO_2$, phenyl, $COOR^1$, $OR^1$ or an aromatic radical containing from 1 to 12 carbon atoms substituted by a $C_{1-6}$ aliphatic group. $R^1$ is a $C_1$-$C_4$ alkyl radical, which can optionally be substituted by one or more halogens, preferably fluorine.

This invention also relates to the formation of mixed acylated polysaccharides, where "mixed" is intended to denote more than one acylating agent A present in the reaction, or a carboxylic acid R'COOH is present in the acylation reaction with $(R"CO)_2O$. In one embodiment, the acylation is carried out with the acylating agent $(R"CO)_2O$ in the presence of R'COOH to give $PS(OH)_{3-x-y}(OCOR')_x(OCOR")_y$. Again, DS (x+y) is usually from 0.5 to 3. R' and R" denote independently from another the same as R above.

An acylating agent A is intended to denote a reactant which is capable of reacting with the hydroxylgroups of the monosaccharide units of the polysaccharide, thereby transferring an acyl group —C(O)R to form the acylated polysaccharide. Acylation agents may be, for example, carboxylic acid anhydrides $(RCO)_2O$, wherein R is defined as above. Preferably, R is —$C_2H_5$, —$CH_2CH_2F$, —$CH_2CHF_2$ or —$CH_2CF_3$, meaning that the carboxylic acid anhydrides are chosen from the group comprising acetic acid anhydride, difluoro acetic acid anhydride and trifluoro acetic acid anhydride. Most preferably, the acylation agent is acetic acid anhydride. Other suitable acylation agents A comprise carboxylic acid halides or carbonylimidazoles. The reaction may be carried out in the presence of at least one acidic compound. In a preferred embodiment, the reaction is carried out in the presence of one or two acidic compounds. In a most preferred embodiment, the reaction is carried out in the presence of two acidic compounds.

The acidic compounds may be chosen from the group consisting of organic and inorganic acidic compounds. Preferably, the acidic compounds comprise carboxylic acids and mineral acids. More preferably, the acidic compounds comprise acetic acid, and a mineral acid preferably selected from sulphuric acid, hydrochloric acid and nitric acid. Most preferably, the acylation reaction is carried out in the presence of acetic acid and sulphuric acid.

In the present invention, the term "polysaccharide" is generally intended to denote a polymer comprising multiple monosaccharide units linked to each other by glycosidic bonds. Examples of suitable polysaccharides are selected from polyglucosans, such as cellulose, the various derivatives of cellulose, such as methyl cellulose, or mixed cellulose ethers, such as methyl hydroxyethyl celluloses, carboxymethyl cellulose, the various salts thereof with sodium, potassium, calcium or ammonium ions, particularly quaternary ammonium ions; cellulose sulfate containing various counterions, for example of sodium, potassium, calcium, ammonium and quaternary ammonium groups; starch, dextrins, glycogen; polyfructosans, such as inulin and graminin; polymannosans, polygalactosans; mixed polysaccharides, such as hemicelluloses, also polyxylosans and polyarabinosans and also heteropolysaccharides, such as gellan, xanthan and pullulan. Preferred starting materials are cellulose and cellulose derivatives, starch and dextrins, particularly preferred starting materials being cellulose, methyl cellulose, ethyl cellulose, hydroxyethyl cellulose, hydroxypropyl cellulose, carboxymethyl cellulose and salts thereof and starch. Preferably, the starting material is cellulose or starch. Most preferably, the starting material is cellulose.

In the present invention, the acylated polysaccharide is manufactured in a process comprising the step of washing the acylated polysaccharide with water. In this washing step, the content of impurities, solvents, excess reactants, excess reagents, by-products and other components contained in the acylated polysaccharide is suitably reduced. The impurities which are separated from the acylated polysaccharide in this step comprise, for example, carboxylic acids, mineral acids, hemicelluloses and lower saccharides such as mono- and di-saccharides. In a most preferred embodiment, celluloseacetate prepared by reacting cellulose with acetic acid anhydride in the presence of acetic acid and sulfuric acid, is washed with water to remove acetic acid, sulfuric acid, hemicelluloses and optional other impurities. In a certain aspect of the invention, the water used in the washing step according to this invention contains from equal to or greater than 0.5 mg/l $Ca^{2+}$-ions. In another aspect of the invention, the $Ca^{2+}$-ion content is equal to or greater than 0.1 mg/l. In a preferred aspect of the invention, the $Ca^{2+}$-ion content is equal to or greater than 0.05 mg/l. Generally, the concentration of $Ca^{2+}$-ions present in the aqueous phase is equal to or lower than 15 mg/l. Preferably, the concentration of $Ca^{2+}$-ions present in the aqueous phase is equal to or lower than 10 mg/l. Even more preferably, the $Ca^{2+}$-ion content in the washing water is equal to or lower than 8 mg/l. In a most preferred embodiment, the $Ca^{2+}$-ion content in the washing water is from 0.05 to 5 mg/l. The process according to the invention allows to avoid precipitation of calcium-salts, for example $CaSO_4$, in the aqueous phase resulting from the washing step. It has been found that by avoiding these precipitates, further treatment of the aqueous phase in nanofiltration or reverse osmosis is possible without notable clogging of the membranes, so that addition of lignosulfates or other surface active agents as described in WO 01/05839 is not necessary.

Therefore the process according to the invention is generally operated in the absence or in the substantial absence of surface active agents, in particular lignosulfates.

"Substantial absence of surface active agents" is understood to denote in particular a concentration of surface active agents in the aqueous phase equal to or lower than 150 ppm, preferably equal to or lower than 100 ppm, and most preferably equal to or lower than 50 ppm.

It should be noted that the tendency to form Ca-salts in the form of precipitates with the $Ca^{2+}$-ions is also, but not solely, dependent on the amount of anions present in the aqueous phase to form salts with the $Ca^{2+}$-ions. Generally, the amount of anion that is present in the aqueous phase according to the present invention is such that the solubility product of the Ca-salt or Ca-salts composed of $Ca^{2+}$-ions and anions in the aqueous phase is not exceeded.

Generally, the concentration of anions present in the aqueous phase is equal to or greater than 10 mg/l. Often this concentration is equal to or greater than 100 mg/l. Preferably, this concentration is equal to or greater than 1000 mg/l.

Generally, the concentration of anions present in the aqueous phase is equal to or lower than 20000 mg/l. Often this concentration is equal to or lower than 18000 mg/l. Preferably, this concentration is equal to or lower than 16000 mg/l.

The above-mentioned anions present in the aqueous phase to form salts with the $Ca^{2+}$-ions may result from the acidic compounds which are generally present in the acylation process. Preferably, the anions comprise $SO_4^{2-}$, $OH^-$, $CO_3^{2-}$, $HCO_3^{2-}$, $PO_4^{3-}$. More preferably, the anion present in the aqueous phase is $SO_4^{2-}$.

In a preferred embodiment of this invention, the aqueous phase recovered from the washing step often comprises carboxylic acids RCOOH, R'COOH and/or R"COOH. R, R' and R" are defined as above. Most preferably, cellulose is acetylated with acetic acid anhydride in the presence of sulphuric acid and acetic acid, and consequently, the aqueous phase comprises acetic acid. In the case that the aqueous phase comprises carboxylic acids RCOOH, R'COOH and/or R"COOH, the concentration of the carboxylic acids RCOOH, R'COOH and/or R"COOH in the aqueous phase recovered from the washing step according to this invention is generally from 1 to 70 wt. % relative to the total weight of the aqueous phase. Preferably, the concentration of the carboxylic acids in said aqueous phase is from 5 to 50 wt. %. A concentration of carboxylic acids RCOOH, R'COOH and/or R"COOH in the aqueous phase from 10 to 40 wt. % is more particularly preferred.

Other solvents, reactants or reagents may also be used in the acylation process according to the present invention, such as organic solvents like dichloromethane or toluene.

In a preferred embodiment of the present invention, the aqueous phase is subjected to at least one nanofiltration or reverse osmosis step. The membranes which are employed in the nanofiltration or reverse osmosis step usually possess a specific retention ability for organic molecules.

"Specific retention ability" in the sense of this invention, expressed in g/mol, is understood to denote the lower molecular weight limit of organic molecules which are substantially retained by the nanofiltration or reverse osmosis. "Substantially retained" in this context is understood to denote that at least 90 wt. %, preferably at least 95 wt. %, more preferably at least 99 wt. % albeit 99.5% of the organic molecules having a molecular weight higher than the specific retention ability are retained by the nanofiltration or reverse osmosis membrane.

In the present invention, the specific retention ability of the nanofiltration or reverse osmosis membrane used is from more than 100 g/mol to more than 300 g/mol. As a result, the amount of molecules having a molecular weight from more than 100 g/mol to more than 300 g/mol, is substantially reduced in the purified aqueous phase after nanofiltration or reversed osmosis, which is also referred to as "permeate". Organic molecules with a molecular weight from equal to or below 100 g/mol to equal to or below 300 g/mol generally pass the nanofiltration or reverse osmosis membrane.

Examples for membranes which can be employed according to the present invention comprise Filmtec BW30 (Dow Chemical), ESPA1 (Hydranautics), XLE (Filmtec), ACM4 TSA (Trisep), Desal DK (Osmonics DESAL), Desal DL (Osmonics DESAL), and AK1 (Osmonics DESAL). Most preferably, the membranes are chosen from Filmtec BW30 (Dow Chemical), ESPA1 (Hydranautics), XLE (Filmtec), Desal DK (Osmonics DESAL), Desal DL (Osmonics DESAL) and AK1 (Osmonics DESAL).

In the nanofiltration or reverse osmosis step according to the present invention, the content of organic molecules with molecular weights from larger than 100 g/mol to larger than 300 g/mol, depending on the employed membrane and the ionic charge of the retained molecules, is reduced in the permeate. Preferably, the amount of impurities with molecular weights from larger than 100 g/mol to larger than 300 g/mol, depending on the employed membrane, is reduced by equal to or greater than 90 wt. %. More preferably, the reduction equal to or greater than 95 wt. %. Most preferably, the reduction is equal to or greater than 99 wt. %, albeit 99.5 wt. %. Particulate impurities may also be retained by the nanofiltration or reverse osmosis membrane. The organic molecules whose content is reduced in the aqueous phase may comprise e.g. hemicelluloses and acylated cellulose fragments. Organic molecules with a molecular weight from equal to or smaller than 100 g/mol to equal to or smaller than 300 g/mol, depending on the employed membrane and the ionic charge of the retained molecules, generally pass through the filtration membrane. The permeate, therefore contains predominantly, apart from water, by-products, excess reagents or reactants of the acylation process with a molecular weight from equal to or smaller than 100 g/mol to equal to or smaller than 300 g/mol, depending on the employed membrane and the ionic charge of the retained molecules. Preferably, the by-product, solvent or excess reagent comprises RCOOH, R'COOH and/or R"COOH, wherein R, R' and R" are defined as above. More preferably, the desired by-product, solvent or excess reagent in the permeate comprises acetic acid, difluoro acetic acid, trifluoro acetic acid. Most preferably, the desired by-product, solvent or excess reagent in the permeate is acetic acid.

Suitably, the filtration conditions for the nanofiltration or reverse osmosis such as flow, pressure and temperature are chosen according to the manufacturer's operating instructions. The membranes should be chosen such that the employed membrane is inert to the components comprised in the given aqueous phase at the given filtration parameters such as temperature.

Prior to the nanofiltration or reverse osmosis step, the aqueous phase may be subjected to a "coarser" filtration step to remove large particles, such as sand-bed filtration, deep bed filtration with special filter cloth or candle filter elements. The desired by-product, solvent or excess reagent comprised in the aqueous phase after nanofiltration or reverse osmosis can be recovered by processes, such as extraction, filtration, drying or distillation, or other recovery and/or purification methods. Preferably, the desired by-product, solvent or excess reagent comprised in the aqueous phase after nanofiltration or reverse osmosis is recovered by extraction and/or distillation Surprisingly, the recovery and/or purification of the by-product, solvent or excess reagent from the permeate according to the present invention can be carried out without notable clogging or fouling of equipment used during the recovery and/or purification process.

The volume ratio of permeate which is separated from the aqueous phase containing the impurities is denoted as "volume reduction" (abbreviated VR), expressed in vol. %. For example, a VR of 60 vol. % denotes that 60% of the aqueous phase has passed the membrane as permeate. According to the present invention, the VR in the filtration step is from 40 vol. % to 99.5 vol. %. Preferably, the VR is from 60 vol. % to 99.5 vol. %. Most preferably, the VR is from 70 vol. % to 98 vol. %.

In a particular aspect of the preferred embodiment of the present invention, carboxylic acids RCOOH, R'COOH and/or R"COOH are recovered in purified form from the permeate. Recovery of the carboxylic acids can be carried out by the techniques described above, in particular by extraction and/or distillation. In a further particular aspect of the preferred embodiment of the present invention, the carboxylic acids RCOOH, R'COOH and/or R"COOH recovered from the permeate in purified form are then converted into acylating agents such as for example the corresponding carboxylic acid anhydrides, carboxylic acid chlorides or carbonylimidazoles. Conversion into acylating agent can be carried out, for example by reaction with a chlorinating agent such as $SO_2Cl$ or, preferably by thermal cracking to ketene and further reaction to carboxylic acid anhydride. More preferably, the carboxylic acids RCOOH, R'COOH and/or R"COOH are converted into the corresponding carboxylic acid anhydrides $(RCO)_2O$, $(R'CO)_2O$ and/or $(R"CO)_2O$. Even more preferably, the recovered carboxylic acids comprise acetic acid, difluoro acetic acid and/or trifluoro acetic acid, which are converted into the corresponding acid anhydrides. Most preferably, the recovered carboxylic acid is acetic acid which is converted to acetic acid anhydride.

The acylating agent manufactured from the recovered carboxylic acid RCOOH, R'COOH and/or R"COOH can be used, for example, as acylating agent in an acylation process of polysaccharides preferably as described herein above.

Should the disclosure of any patents, patent applications, and publications which are incorporated herein by reference conflict with the description of the present application to the extent that it may render a term unclear, the present description shall take precedence.

The examples hereafter are intended to illustrate the invention in a non-limitative manner.

EXAMPLE 1

Cellulose was pre-treated in acetic acid with sulphuric acid as described in A. Hummel, "Industrial processes", Macromolecular Symposia, 2004, Vol 208(1), p. 61-80. The activated cellulose was then reacted with a mixture of acetic acid and acetic acid anhydride at a temperature of 45-85° C. After completed reaction, the reaction mixture was quenched with a solution of 60 wt. % of acetic acid in water. The $Ca^{2+}$-content of the water used for the aqueous acid solution was 4.6 mg/l. The reaction mixture was then poured into water containing 4.6 mg/l $Ca^{2+}$-ions and 16 wt. % acetic acid, and the cellulose acetate precipitates. The precipitated cellulose acetate was washed with water containing 4.6 mg/l $Ca^{2+}$-ions and dried. The combined aqueous phase from quenching, precipitation and washing contained approximately 30% acetic acid. The aqueous phase was filtered with a 5 μm filter and then subjected to batch mode reverse osmosis using an AK4040 membrane (Osmonics Desal). A VR of 96.3% was achieved, while no decrease in permeate quality or increase of operation pressure or differential pressure of the 5 μm filter, which would have indicated membrane or filter blockage, was observed. A foam test was performed to control the efficiency of the reverse osmosis: 1 part of permeate was diluted with 4 parts of water and shaken. The foam standing time of the permeate throughout the reverse osmosis step at all VR values was 5 sec, whereas the foam standing time of the aqueous phase before reverse osmosis was more than 300 seconds, indicating an efficient removal of organic impurities. The permeate was subjected to liquid/liquid extraction with diethylether and subsequent distillation to yield glacial acetic acid. During the extraction and distillation, no clogging, encrusting or fouling of the equipment was observed.

The invention claimed is:

1. A process for manufacturing an acylated polysaccharide and recovering a permeate containing carboxylic acid comprising:
   (a) reacting a polysaccharide with an acylating agent to produce an acylated polysaccharide,
   wherein the polysaccharide is cellulose, methyl cellulose, ethyl cellulose, hydroxyethyl cellulose, hydroxypropyl cellulose, carboxymethyl cellulose, and sodium, potassium, calcium or ammonium salts of cellulose, methyl cellulose, ethyl cellulose, hydroxyethyl cellulose, hydroxypropyl cellulose, carboxymethyl cellulose or starch,
   wherein the acylation agent comprises
      at least one organic acidic compound selected from the group consisting of acetic anhydride and acetic acid, and
      a mineral acid comprising sulphuric acid;
   (b) quenching, precipitating and washing the acylated polysaccharide with water containing from 0.05 to 8 mg/l $Ca^{2+}$-ions; and
   (c) recovering the washed acylated polysaccharide and a combined aqueous phase from the quenching, precipitating and washing containing carboxylic acid from step (b), wherein concentration of carboxylic acid in the combined aqueous phase is 5 to 40 wt. %,
   wherein the combined aqueous phase is treated by nanofiltration or reverse osmosis to recover a permeate containing carboxylic acid and wherein the process is carried out in the substantial absence of a surface active substance, wherein concentration of the surface-active substance in the combined aqueous phase is equal to or lower than 150 ppm, wherein there is an absence of lignosulfates, wherein all water used to wash the acylated polysaccharide contains from 0.05 to 8 mg/l $Ca^{2+}$-ions;
   wherein the combined aqueous phase contains from 10 to 20000 mg/l $SO_4^{2-}$-ions.

2. The process of claim 1, wherein the acylating agent is acetic acid anhydride.

3. The process according to claim 1, wherein the polysaccharide is cellulose or starch.

4. The process according to claim 1, wherein step (a) is carried out in the presence of at least one acidic compound.

5. The process according to claim 1, wherein the concentration of the surface-active substance in the aqueous phase is equal to or lower than 105 ppm.

6. The process according to claim 1, wherein the aqueous phase before filtration contains from 10 to 40 wt. % acetic acid, and from 10 to 20000 mg/l $SO_4^{2-}$-ions.

7. The process according to claim 6, wherein the aqueous phase further comprises organic impurities with a minimal molecular weight from more than 100 g/mol to more than 300 g/mol.

8. The process according to claim 1, wherein the nanofiltration or reverse osmosis filtration is carried out employing a membrane with a capacity to filter organic impurities with a molecular weight from more than 100 g/mol to more than 300 g/mol.

9. The process according to claim 1, wherein the volume reduction in the nanofiltration or reverse osmosis is from 50% to 99%.

10. The process according to claim 1, wherein the concentration of surface active substance in the aqueous phase is equal to or lower than 50 ppm, wherein anions present in the combined aqueous phase to form salts with the $Ca^{2+}$ ions consist of at least one member selected from the group consisting of $SO_4^{2-}$, $CO_3^{2-}$, $HCO_3^{2-}$, and $PO_4^{3-}$.

11. The process according to claim 4, wherein the at least one acidic compound is selected from the group consisting of acetic acid and sulfuric acid.

12. The process according to claim 1, wherein the nanofiltration or reverse osmosis filtration is carried out employing a membrane with a capacity to filter organic impurities with a molecular weight of more than 300 g/mol.

13. The process according to claim 1, wherein the process is carried out in the absence of surface-active substance.

14. The process according to claim 1, wherein the polysaccharide (PS) has formula $PS(OH)_{3-x}$ and reacts with the acylation agent to form the acylated polysaccharide of formula $PS(OH)_{3-x}(OCOR)_x$, wherein x denotes the degree of substitution of the hydroxyl groups in the polysaccharide and is from 0.5 to 3.

15. The process according to claim 1, wherein the polysaccharide is cellulose.

16. The process according to claim 1,
   wherein the water for quenching, precipitating and washing the acetylated polysaccharide contains from 0.05 to 5 mg/l $Ca^{2+}$-ions,
   wherein the polysaccharide is cellulose, wherein the acylation agent comprises sulphuric acid;
   wherein the carboxylic acid comprises acetic acid;
   wherein the polysaccharide and the acylation agent react to produce a reaction mixture comprising the acylated cellulose;
   wherein the reaction mixture was quenched with a solution of acetic acid and water, wherein the acylated cellulose was precipitated from the quenched reaction mixture;
   wherein the aqueous phase before filtration contains from 5 to 40 wt. % acetic acid, from 0.05 to 5 mg/l $Ca^{2+}$-ions, and from 10 to 16000 mg/l $SO_4^{2-}$-ions,
   wherein the nanofiltration or reverse osmosis filtration is carried out employing a membrane with a capacity to filter organic impurities with a molecular weight from more than 100 g/mol to more than 300 g/mol.

17. A process for recovering acylated polysaccharide and recovering a permeate containing carboxylic acid, the process comprising:
   (a) reacting a polysaccharide with an acylating agent to produce an acylated polysaccharide, wherein the polysaccharide is cellulose, methyl cellulose, ethyl cellulose, hydroxyethyl cellulose, hydroxypropyl cellulose, carboxymethyl cellulose, and sodium, potassium, calcium or ammonium salts of cellulose, methyl cellulose, ethyl cellulose, hydroxyethyl cellulose, hydroxypropyl cellulose, carboxymethyl cellulose or starch, wherein the acylation agent comprises at least one organic acidic compound selected from the group consisting of acetic anhydride and acetic acid, and a mineral acid comprising sulphuric acid;
   (b) quenching, precipitating and washing the acylated polysaccharide with water containing from 0.05 to 8 mg/l $Ca^{2+}$-ions; and
   (c) recovering the washed acylated polysaccharide and a combined aqueous phase from the quenching, precipitating and washing containing carboxylic acid from step (b), wherein concentration of carboxylic acid in the combined aqueous phase is 5 to 40 wt. %;
(d) treating the combined aqueous phase by nanofiltration or reverse osmosis to recover a permeate containing carboxylic acid to provide a purified aqueous phase containing carboxylic acid, wherein the process is carried out in the substantial absence of a surface active substance, wherein concentration of the surface-active substance in the combined aqueous phase is equal to or lower than 150 ppm, wherein there is an absence of lignosulfates; and
(e) subjecting the purified aqueous phase to at least one further purification step,
wherein all water used to wash the acylated polysaccharide contains from 0.05 to 8 mg/l $Ca^{2+}$-ions;
wherein the combined aqueous phase contains from 10 to 20000 mg/l $SO_4^{2-}$-ions.

18. The process according to claim 17, wherein the purification step is selected from the group consisting of extraction, drying, washing, distillation, or combinations thereof.

19. The process according to claim 17, wherein the water for quenching, precipitating and washing the acetylated polysaccharide contains from 0.05 to 5 mg/l $Ca^{2+}$-ions.

20. A process for the acetylation of polysaccharides and recovering a permeate containing carboxylic acid, the process comprising:
(a) reacting a polysaccharide with acetic anhydride to produce an acetylated polysaccharide, wherein the polysaccharide is cellulose, methyl cellulose, ethyl cellulose, hydroxyethyl cellulose, hydroxypropyl cellulose, carboxymethyl cellulose, and sodium, potassium, calcium or ammonium salts of cellulose, methyl cellulose, ethyl cellulose, hydroxyethyl cellulose, hydroxypropyl cellulose, carboxymethyl cellulose or starch, wherein the acylation agent comprises at least one organic acidic compound selected from the group consisting of acetic anhydride and acetic acid, and a mineral acid comprising sulphuric acid;
(b) quenching, precipitating and washing the acetylated polysaccharide with water containing from 0.05 to 8 mg/l $Ca^{2+}$-ions; and
(c) recovering the washed acetylated polysaccharide and a combined aqueous phase from the quenching, precipitating and washing containing carboxylic acid from step (b), wherein concentration of carboxylic acid in the combined aqueous phase is 5 to 40 wt. %;
(d) treating the combined aqueous phase by nanofiltration or reverse osmosis to recover a permeate containing acetic acid to provide a purified aqueous phase containing acetic acid, wherein the process is carried out in the substantial absence of a surface active substance, wherein concentration of the surface-active substance in the combined aqueous phase is equal to or lower than 150 ppm, wherein there is an absence of lignosulfates; and
(e) subjecting the purified aqueous phase to at least one further purification step
(f) converting the acetic acid obtained in step (e) into acetic anhydride; and
(g) reacting a polysaccharide with the acetic anhydride obtained in step (f),
wherein all water used to wash the acylated polysaccharide contains from 0.05 to 8 mg/l $Ca^{2+}$-ions;
wherein the combined aqueous phase contains from 10 to 20000 mg/l $SO_4^{2-}$-ions.

21. The process of claim 20, wherein the polysaccharide is cellulose.

22. The process of claim 20, wherein the acetylation is further carried out in the presence of at least one acidic compound selected from the group consisting of acetic acid and sulfuric acid.

23. The process according to claim 20, wherein the water for quenching, precipitating and washing the acetylated polysaccharide contains from 0.05 to 5 mg/l $Ca^{2+}$-ions.

24. A process for manufacturing an acylated polysaccharide and recovering a permeate containing carboxylic acid comprising:
(a) reacting a polysaccharide with an acylating agent to produce an acylated polysaccharide;
(b) quenching, precipitating and washing the acylated polysaccharide with water containing from 0.05 to 8 mg/l $Ca^{2+}$-ions; and
(c) quenching, precipitating and recovering the washed acylated polysaccharide and a combined aqueous phase from the quenching, precipitating and washing containing carboxylic acid from step (b);
wherein the polysaccharide (PS) has formula $PS(OH)_{3-x}$ and reacts with the acylation agent to form the acylated polysaccharide of formula $PS(OH)_{3-x}(OCOR)_x$, wherein x denotes the degree of substitution of the hydroxyl groups in the polysaccharide and is from 0.5 to 3;
wherein the acylation agent comprises at least one member selected from the group consisting of carboxylic acid anhydrides of formula $(RCO)_2O$, carboxylic acids, carboxylic acid halides, and carbonylimidazoles, and the acylation agent comprises mineral acid comprising sulfuric acid;
wherein R of the acylation agent and the acylated polysaccharide is an aliphatic or cycloaliphatic radical containing 1 to 18 carbon atoms, an araliphatic radical containing 7 to 12 carbon atoms, an aromatic radical containing 6 to 12 carbon atoms; wherein R may be optionally substituted by one or more of halogens, $NO_2$, phenyl, $COOR^1$, $OR^1$ or an aromatic radical containing from 1 to 12 carbon atoms substituted by a $C_{1-6}$ aliphatic group, wherein $R^1$ is a $C_1$-$C_4$ alkyl radical optionally substituted by one or more halogens;
wherein the process is carried out in the substantial absence of a surface active substance,
wherein the combined aqueous phase is treated by nanofiltration or reverse osmosis to recover a permeate containing carboxylic acid and wherein the process is carried out in the substantial absence of a surface active substance, wherein concentration of the surface-active substance in the combined aqueous phase is equal to or lower than 150 ppm, wherein there is an absence of lignosulfates;
wherein all water used to wash the acylated polysaccharide contains from 0.05 to 8 mg/l $Ca^{2+}$-ions;
wherein the combined aqueous phase contains from 10 to 20000 mg/l $SO_4^{2-}$-ions.

* * * * *